United States Patent
Yamanaka et al.

(10) Patent No.: US 10,294,351 B2
(45) Date of Patent: May 21, 2019

(54) FLAMEPROOFING AGENT FOR FIBERS

(71) Applicants: TEIJIN LIMITED, Osaka (JP); MARUBISHI OIL CHEMICAL CO., LTD., Osaka (JP)

(72) Inventors: Katsuhiro Yamanaka, Tokyo (JP); Tsuyoshi Takeda, Tokyo (JP); Kuniaki Kondo, Osaka (JP); Masaki Haruyoshi, Osaka (JP)

(73) Assignees: TEIJIN LIMITED, Osaka (JP); MARUBISHI OIL CHEMICAL CO., LTD., Osaka (JP)

( * ) Notice: Subject to any disclaimer, the term of this patent is extended or adjusted under 35 U.S.C. 154(b) by 246 days.

(21) Appl. No.: 14/385,265

(22) PCT Filed: Mar. 26, 2013

(86) PCT No.: PCT/JP2013/059800
§ 371 (c)(1),
(2) Date: Sep. 15, 2014

(87) PCT Pub. No.: WO2013/147294
PCT Pub. Date: Oct. 3, 2013

(65) Prior Publication Data
US 2015/0038036 A1  Feb. 5, 2015

(30) Foreign Application Priority Data

Mar. 29, 2012  (JP) ................. 2012-075415

(51) Int. Cl.
| | |
|---|---|
| *C08K 5/527* | (2006.01) |
| *D06M 13/288* | (2006.01) |
| *C07F 9/6571* | (2006.01) |
| *D06M 13/282* | (2006.01) |
| *D06M 11/44* | (2006.01) |
| *D06M 11/45* | (2006.01) |
| *D06M 11/46* | (2006.01) |
| *D06M 11/69* | (2006.01) |
| *D06M 11/72* | (2006.01) |
| *D06M 11/74* | (2006.01) |
| *D06M 11/76* | (2006.01) |
| *D06M 11/82* | (2006.01) |
| *D06M 15/43* | (2006.01) |
| *D06N 3/00* | (2006.01) |

(52) U.S. Cl.
CPC ........ *C08K 5/527* (2013.01); *C07F 9/657181* (2013.01); *D06M 11/44* (2013.01); *D06M 11/45* (2013.01); *D06M 11/46* (2013.01); *D06M 11/69* (2013.01); *D06M 11/72* (2013.01); *D06M 11/74* (2013.01); *D06M 11/76* (2013.01); *D06M 11/82* (2013.01); *D06M 13/282* (2013.01); *D06M 13/288* (2013.01); *D06M 15/43* (2013.01); *D06N 3/0059* (2013.01); *D06M 2200/30* (2013.01); *Y10T 442/2672* (2015.04)

(58) Field of Classification Search
CPC .......... C07F 9/657181; D06M 13/288; D06M 2200/30; Y10T 442/2672
USPC ................................. 442/141, 136
See application file for complete search history.

(56) References Cited

U.S. PATENT DOCUMENTS

| | | | |
|---|---|---|---|
| 3,760,037 A | * | 9/1973 | Yoshizawa ............ C08G 79/04 162/159 |
| 4,154,721 A | | 5/1979 | Valdiserri et al. |
| 4,178,281 A | | 12/1979 | Horn et al. |
| 2003/0193045 A1 | | 10/2003 | Takeuchi et al. |

(Continued)

FOREIGN PATENT DOCUMENTS

| | | |
|---|---|---|
| CN | 101070458 | 11/2007 |
| EP | 1 369 464 | 12/2003 |
| EP | 1 586 576 | 10/2005 |

(Continued)

OTHER PUBLICATIONS

European Search Report dated Jan. 7, 2015 in European Application No. 13769259.6.

(Continued)

*Primary Examiner* — Vincent Tatesure
(74) *Attorney, Agent, or Firm* — Wenderoth, Lind & Ponack, L.L.P.

(57) ABSTRACT

A flameproofing agent for fibers which has high flameproofness and excellent physical properties (light resistance, heat resistance, texture), a process for manufacturing a flameproof fiber product and a flameproof fiber product.
The flameproofing agent comprises an organic phosphorus compound (component A) represented by the following formula (1).

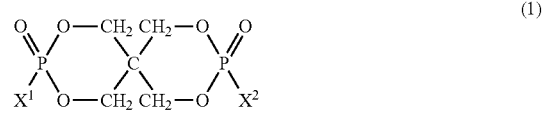

(1)

(In the above formula, $X^1$ and $X^2$ are the same or different and each an aromatic substituted alkyl group represented by the following formula (2).)

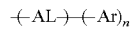

(2)

(In the above formula, AL is a branched or linear aliphatic hydrocarbon group having 1 to 5 carbon atoms, Ar is a phenyl group, naphthyl group or anthryl group all of which may have a substituent, "n" is an integer of 1 to 3, and Ar may be bonded to any carbon atom contained in AL.)

9 Claims, No Drawings

(56) References Cited

U.S. PATENT DOCUMENTS

2006/0116526 A1 6/2006 Tanabe et al.
2009/0227713 A1 9/2009 Kyoda et al.

FOREIGN PATENT DOCUMENTS

| | | |
|---|---|---|
| EP | 1 925 622 | 5/2008 |
| EP | 2 287 253 | 2/2011 |
| GB | 1 515 223 | 6/1978 |
| JP | 10-212-669 | 8/1998 |
| JP | 2002-220782 | 8/2002 |
| JP | 2003-306679 | 10/2003 |
| JP | 3484490 | 10/2003 |
| JP | 2006-063125 | 3/2006 |
| JP | 2006-83491 | 3/2006 |
| WO | 2004/060900 | 7/2004 |
| WO | WO2004060900 A1 * | 7/2004 |
| WO | 2007/032277 | 3/2007 |
| WO | 2007/097146 | 8/2007 |
| WO | 2009/145341 | 12/2009 |

OTHER PUBLICATIONS

International Preliminary Report on Patentability dated Oct. 1, 2014 in International (PCT) Application No. PCT/JP2013/059800.
International Search Report dated May 14, 2013 in International (PCT) Application No. PCT/JP2013/059800.

* cited by examiner

FLAMEPROOFING AGENT FOR FIBERS

TECHNICAL FIELD

The present invention relates to a flameproofing agent for fibers which has high flameproofness and excellent physical properties and a flameproof fiber product.

BACKGROUND ART

In recent years, a large number of fibers have been used in interior materials for automobiles, airplanes, railroads and buildings and filter materials, and fiber materials such as synthetic fibers including polyester, nylon, acrylonitrile and polypropylene fibers, cellulose-based fibers including rayon, cotton and hemp fibers, and animal fibers including woolen, silk and feather fibers have been used alone or in combination.

Since fiber products comprising these fibers have a defect that they are highly combustible, flameproofing performance is required for these products. For example, flame-retardant fibers are used in some fields such as uniforms for airplane pilots, and post-processing flameproofing is generally carried out on the fibers from the viewpoint of cost.

Typical examples of post-processing flameproofing include a method in which a flameproofing agent is directly adhered to a fiber product and a method in which a flameproofing agent is added to synthetic fiber binders and adhered as a flameproofing binder. These methods are generally employed for sheets for chair upholstery for automobiles, airplanes and railcars or backing for carpets. Especially in the latter flameproofing method, it is necessary to flameproof not only fibers but also a synthetic resin binder used in combination.

A halogen-based compound or a combination of a halogen-based compound and antimony oxide has been used as a flameproofing agent. However, in recent years, demand for flameproofing without using a halogen-based flameproofing agent has been growing due to environment conservation and the harmful effect of a gas generated at the time of combustion. As a halogen-free flameproofing agent, there are known a large number of flameproofing agents such as ammonium phosphate, ammonium sulfamate, ammonium sulfate, pyrobate, boric acid, aluminum hydroxide, magnesium hydroxide and phosphoric acid esters.

However, when the flameproofing agent is added in an amount required for producing a flameproofing effect, a water-soluble flameproofing agent causes problems such as the thickening of a synthetic resin emulsion, the occurrence of destruction (gum-up), the reduction of the strength of a resin film, the degradation of heat resistance and the deterioration of texture. Since ammonium polyphosphate which is halogen-free and has a flameproofing effect relatively has solubility in water, it elutes into water under conditions under which water resistance is required, thereby causing problems with the physical properties and flameproofness of a product. Further, even ammonium polyphosphate which is capsulated with an improved resin is unsatisfactory in terms of water resistance. Therefore, a flameproofing method which provides satisfactory flameproofness and physical properties without using a halogen-based flameproofing agent is not provided and the development of such a method is desired (patent documents 1 to 3).
(Patent Document 1) JP-A 10-212669
(Patent Document 2) JP-A 2002-220782
(Patent Document 3) Japan Patent No. 3484490

DISCLOSURE OF THE INVENTION

It is an object of the present invention to provide a flameproofing agent for fibers having high flameproofness and excellent physical properties (light resistance, heat resistance, texture), a process for manufacturing a flameproof fiber product and a flameproof fiber product obtained by the process.

The inventors of the present invention conducted intensive studies to attain the above objects and found that an organic phosphorus compound (component A) represented by the following formula (1) which is insoluble or hardly soluble in water has high flameproofness and excellent physical properties (light resistance, heat resistance, texture) as a flameproofing agent for fibers.

That is, the present invention is a flameproofing agent for fibers which comprises an organic phosphorus compound (component A) represented by the following formula (1). Further, the present invention is a process for manufacturing a flameproof fiber product, comprising the step of adhering a flameproofing agent for fibers comprising 1 to 300 parts by weight of an organic phosphorus compound (component A) represented by the following formula (1) based on 100 parts by weight of a dispersant to a fiber product in an amount of 3 to 150 wt % as a solid content. Still further, the present invention includes a flameproof fiber product obtained by this manufacturing process.

The present invention is also a method of improving the weatherability of a flameproof fiber product obtained by adhering a flameproofing agent to a fiber product, wherein (i) the method comprises the step of adhering the flameproofing agent to the fiber product in an amount of 3 to 150 wt % as a solid content; and (ii) the flameproofing agent comprises 1 to 300 parts by weight of an organic phosphorus compound (component A) represented by the following formula (1) based on 100 parts by weight of a dispersant.

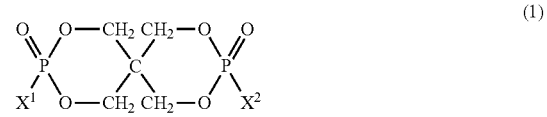
(1)

(In the above formula, $X^1$ and $X^2$ are the same or different and each an aromatic substituted alkyl group represented by the following formula (2).)

(2)

(In the above formula, AL is a branched or linear aliphatic hydrocarbon group having 1 to 5 carbon atoms, Ar is a phenyl group, naphthyl group or anthryl group all of which may have a substituent, "n" is an integer of 1 to 3, and Ar may be bonded to any carbon atom contained in AL.)

BEST MODE FOR CARRYING OUT THE INVENTION

A detailed description is subsequently given of a flameproofing agent for fibers, a method of flameproofing a fiber product and a flameproof fiber product obtained thereby according to the present invention.

(Organic Phosphorus Compound (Component A))

In the present invention, the organic phosphorus compound (component A) is a compound represented by the following formula (1).

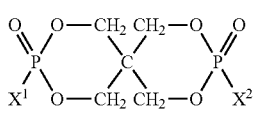
(1)

(In the above formula, $X^1$ and $X^2$ are the same or different and each an aromatic substituted alkyl group represented by the following formula (2).)

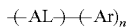
(2)

In the above formula, AL is a branched or linear aliphatic hydrocarbon group having 1 to 5 carbon atoms. Examples of the aliphatic hydrocarbon group include alkanediyl groups, alkanetriyl groups and alkanetetrayl groups.

More specifically, alkylene groups having 1 to 5 carbon atoms such as methylene group, ethylene group, trimethylene group, isopropyldiyl group, butylene group and pentylene group are included. Alkanetriyl groups having 1 to 5 carbon atoms such as methanetriyl group, ethanetriyl group, propanetriyl group, butanetriyl group and pentanetriyl group are also included. Alkanetetrayl groups having 1 to 5 carbon atoms such as methanetetrayl group, ethanetetrayl group, propanetetrayl group, butanetetrayl group and pentanetetrayl group are further included.

Ar is a phenyl group, naphthyl group or anthryl group all of which may have a substituent. Examples of the substituent include alkyl groups having 1 to 5 carbon atoms such as methyl group, ethyl group and propyl group, and halogen atoms such as fluorine atom, chlorine atom and bromine atom.

Ar may be bonded to any carbon atom contained in AL. "n" is an integer of 1 to 3.

The organic phosphorus compound (component A) is preferably a compound represented by the following formula (3).

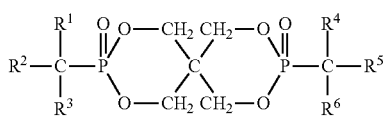
(3)

In the above formula, $R^2$ and $R^5$ may be the same or different and each a phenyl group, naphthyl group or anthryl group all of which may have a substituent. Examples of the substituent include alkyl groups having 1 to 5 carbon atoms such as methyl group, ethyl group and propyl group, and halogen atoms such as fluorine atom, chlorine atom and bromine atom.

$R^1$, $R^3$, $R^4$ and $R^6$ may be the same or different and each a substituent selected from hydrogen atom, branched or linear alkyl group having 1 to 4 carbon atoms, and phenyl group, naphthyl group and anthryl group all of which may have a substituent. Examples of the alkyl group having 1 to 4 carbon atoms include methyl group, ethyl group, propyl group, isopropyl group, butyl group and t-butyl group. Examples of the substituent of the phenyl group, naphtyl group and anthryl group include alkyl groups having 1 to 5 carbon atoms such as methyl group, ethyl group and propyl group, and halogen atoms such as fluorine atom, chlorine atom and bromine atom.

Further, an organic phosphorus-based compound represented by the following formula (9) is preferred.

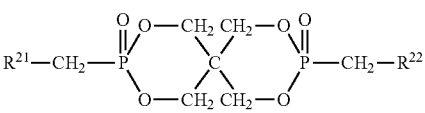
(4)

In the above formula, $R^{21}$ and $R^{22}$ are the same or different and each a phenyl group, naphthyl group or anthryl group all of which may have a substituent in the aromatic ring, out of which phenyl group is preferred.

The hydrogen atom of the aromatic ring of the phenyl group, naphthyl group or anthryl group represented by $R^{21}$ and $R^{22}$ may be substituted. Examples of the substituent include methyl, ethyl, propyl, butyl or aryl group having 6 to 14 carbon atoms and a bond of the aromatic ring via an oxygen atom, sulfur atom or aliphatic hydrocarbon group having 1 to 4 carbon atoms.

The organic phosphorus compound (component A) represented by the above formula (1) produces an extremely excellent flameproofing effect while it retains water resistance as a flameproofing agent for fibers. As far as the inventors of the present invention know, it has been extremely difficult for a halogen-free flameproofing agent for fibers to achieve water resistance and flameproofness at the same time, and there have been a large number of practical problems to be solved.

However, according to the present invention, surprisingly, the above organic phosphorus compound (component A) makes it easy to achieve water resistance and high flameproofness at the same time and makes it possible to provide an excellent flameproof fiber product as a flameproofing agent for fibers.

In the present invention, a flameproofing agent except for the component A and/or other additives may be used for the purpose of reducing the amount of the component A and improving the flame retardancy, physical properties and chemical properties of a fiber product and other purposes in addition to the component A, as a matter of course. The other components will be described hereinafter.

Although the organic phosphorus compound (component A) as the flameproofing agent for fibers of the present invention is represented by the above formula (1), the most preferred typical compound is represented by the following formula (1-a).

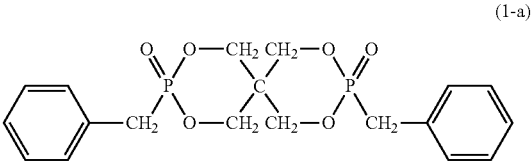 [SMILES: O=P1(Cc2ccccc2)OCC2(CO1)COP(=O)(Cc1ccccc1)OC2]
(1-a)

Since the organic phosphorus compound (component A) represented by the above formula (1) has extremely low solubility in water as compared with ammonium polyphosphate and capsulated ammonium polyphosphate which are generally used as halogen-free flameproofing agents, it can provide flameproofness and water resistance. The solubility in 80° C. hot water of the organic phosphorus compound of the formula (1-a) is not more than 0.5%, that of ammonium polyphosphate is 80.8% and that of silica-coated ammonium polyphosphate is 12.8%.

A description is subsequently given of a process for synthesizing the organic phosphorus compound (component A) of the present invention. The component A may be produced by a process other than the process explained below.

The component A is obtained by reacting pentaerythritol with phosphorus trichloride, treating the oxidated reaction product with an alkali metal compound such as sodium methoxide and then reacting the treated reaction product with aralkyl halide.

It can also be obtained by reacting pentaerythritol with aralkylphosphonic acid dichloride or by reacting pentaerythritol with phosphorus trichloride, reacting the obtained product with aralkyl alcohol and carrying out Arbuzov rearrangement at a high temperature. The latter reaction is disclosed, for example, by U.S. Pat. No. 3,141,032, JP-A 54-157156 and JP-A 53-39698.

The specific process for synthesizing the component A will be explained hereinbelow, this process is simply for explanation, and the component A used in the present invention may be synthesized not only by this synthesizing process but also its modified or other synthesizing processes. The synthesizing process will be explained more specifically in Preparation Example which is given hereinafter.

(I) Organic Phosphorus Compound of the Formula (1-a) Contained in Component A;

This organic phosphorus compound can be obtained by reacting pentaerythritol with phosphorus trichloride, treating the reaction product oxidated by tertiary butanol with sodium methoxide and reacting the treated product with benzyl bromide.

Alternatively, the organic phosphorus compound is obtained by reacting pentaerythritol with phosphorus trichloride and heating a reaction product between the obtained product and benzyl alcohol in the presence of catalyst.

The above-described component A has an acid value of not more than 0.7 mgKOH/g, preferably not more than 0.5 mgKOH/g. By using the component A having an acid value within this range, a flameproofing agent and a flameproof fiber product both of which are excellent in flameproofness, hue and heat stability are obtained. The component A having an acid value of not more than 0.4 mgKOH/g is most preferred. The acid value means the amount (mg) of KOH required for neutralizing an acid component contained in 1 g of a sample (component A).

Further, the component A has an HPLC purity of preferably at least 90%, more preferably at least 95%. This pure component A is preferred as it is excellent in the flameproofness, hue and heat stability of a processing agent and a flameproof fiber product. The HPLC purity of the component A can be measured effectively by using the following method.

The Develosil ODS-7 having a length of 300 mm and a diameter of 4 mm of Nomura Chemical Co., Ltd. was used as a column, and the column temperature was 40° C. A mixed solution of acetonitrile and water in a volume ratio of 6:4 was used as a solvent, and 5 µl of the solution was injected. A UV-260 nm detector was used.

Although the method of removing impurities contained in the component A is not particularly limited, a method in which repulp cleaning (cleaning with a solvent and filtering are repeated several times) with a solvent such as water or methanol is carried out is the most effective and financially advantageous.

Further, the average particle diameter of the component A is preferably 5 to 100 µm, more preferably 10 to 50 µm.

(Dispersant)

In the present invention, the organic phosphorus compound (component A) is used as a flameproofing agent for fibers while it is mixed with a dispersant. As for the mixing ratio of the dispersant and the organic phosphorus compound (component A), the amount of the organic phosphorus compound (component A) is preferably 1 to 300 parts by weight, more preferably 5 to 200 parts by weight and much more preferably 10 to 100 parts by weight based on 100 parts by weight of the dispersant. When the amount of the organic phosphorus compound as the component A is smaller than 1 part by weight, the flameproofing effect may become unsatisfactory and when the amount is larger than 300 parts by weight, the formation of a resin film tends to become difficult, and a fiber product may deteriorate in quality.

As the dispersant, water, an organic solvent or a resin (including a solution, emulsion and latex) is preferably used, and a resin solution, resin emulsion or latex is more preferably used.

When a resin solution, resin emulsion or latex is used as the dispersant, the organic phosphorus compound (component A) is used in an amount of preferably 5 to 300 parts by weight, more preferably 10 to 200 parts by weight and much more preferably 20 to 100 parts by weight based on 100 parts by weight of the solid component. When the amount of the component A is smaller than 5 parts by weight, the flameproofing effect may become unsatisfactory and when the amount is larger than 300 parts by weight, the formation of a binder resin film tends to become difficult and a fiber product may deteriorate in quality.

Examples of the resin used in the present invention include polyacrylic acid esters, polymethacrylic acid esters, copolymers of an acrylic acid ester and/or methacrylic acid ester and a vinyl-based monomer or olefinic monomer, other olefinic monomers, polymers, copolymers and mixtures of a vinyl-based monomer, polyurethane, polyvinyl acetate, ethylene-vinyl acetate copolymer, polyesters, SBR (styrene butadiene rubber), vinyl chloride and vinylidene chloride.

The preferred range of the amount of the component A is determined according to the desired level of flameproofness, the type of the binder resin component, the type of a fiber and the shape of a fiber product. Optionally, other components may be used as long as the object of the present invention is not impaired. The amount of the component A can be changed by using another flameproofing agent and a flameproofing aid. In most cases, the amount of the component A can be reduced by using these.

The process for producing the flameproofing agent of the present invention is not particularly limited as long as these components can be uniformly mixed and stirred. For example, after predetermined component raw materials are mixed together, they are stirred by means of dispersion/milling machine such as a homogenizer, ball mill or bead mill, thereby making it possible to prepare the flameproofing agent of the present invention.

(Surfactant)

To enhance the dispersibility and emulsifiability of the organic phosphorus compound (component A), a known surfactant may be optionally used. At least one selected from anionic surfactants and nonionic surfactants is preferably used.

The anionic surfactants include higher alcohol sulfuric acid ester salts, polyoxyethylene alkylphenyl sulfuric acid ester salts, sulfated fatty ester salts, alkylbenzene sulfonic acid salts, alkyl naphthalene sulfonic acid salts and higher alcohol phosphoric acid ester salts.

The nonionic surfactants include polyoxyalkylene natural fat alkyl ethers, polyoxyalkylene higher alcohol alkyl ethers, polyoxyalkylene alkylphenyl ethers and polyhydric alcohol fatty acid esters.

The amount of the surfactant is not particularly limited and can be suitably set in consideration of the type of the dispersant in use and the degree of dispersion or emulsification. For example, the surfactant is contained in an amount of preferably 1 to 30 parts by weight, more preferably 3 to 20 parts by weight based on 100 parts by weight of the dispersant.

(Stabilizer)

When the organic phosphorus compound as the component A precipitates, a dispersion stabilizer or an emulsification stabilizer (both are collectively referred to as "stabilizer") may be used. At least one selected from sodium polyacrylate, polyvinyl alcohol, polyvinyl pyrrolidone, methyl cellulose, carboxymethyl cellulose, hydroxyethyl cellulose, xanthan gum and starch paste is used as the dispersion stabilizer. Examples of the emulsification stabilizer include triglycerides such as castor oil and canola oil; esters such as phosphoric acid esters and phthalic acid esters; and higher alcohols. By adding these stabilizers, the viscosity of a flameproofing agent is adjusted to stabilize a homogeneous processing liquid.

The content of the stabilizer is not particularly limited and can be suitably set in consideration of the type of the stabilizer in use and the degree of dispersion or emulsification. For example, the stabilizer is used in an amount of preferably 0.1 to 10 parts by weight, more preferably 1 to 3 parts by weight based on 100 parts by weight of the dispersant.

(Another Flameproofing Agent)

A flameproofing agent (to be referred to as "combined flameproofing agent" hereinafter) other than the organic phosphorus compound (component A) of the present invention may be optionally used in combination with the flameproofing agent of the present invention.

The combined flameproofing agent is not particularly limited but examples thereof include inorganic combined flameproofing agents such as aluminum hydroxide, titanium oxide, zinc oxide, swellable graphite, magnesium hydroxide, calcium carbonate, zinc borate, ammonium polyphosphate and red phosphorus, and organic combined flameproofing agents such as melamine, melamine polyphosphate, melamine cyanurate and phosphoric acid ester-based compounds. The combined flameproofing agents may be used alone or in combination of two or more.

The phosphoric acid ester-based compounds as the above combined flameproofing agent include trioctyl phosphate, triphenyl phosphate, tricresyl phosphate, trixylenyl phosphate, cresyldiphenyl phosphate, cresyl di2,6-xylenyl phosphate, isopropylphenyl phosphate, tert-butylphenyl phosphate, biphenyldiphenyl phosphate, naphthyldiphenyl phosphate, resorcinol bis(diphenylphosphate), resorcinol bis(dixylenylphosphate), bisphenol A bis(diphenylphosphate), tris(chloropropyl)phosphate, tris(dichloropropyl)phosphate and tris(tribromoneopentyl)phosphate.

Out of these combined flameproofing agents, melamine polyphosphate and melamine cyanurate are particularly preferred.

The amount of the combined flameproofing agent is preferably 1 to 200 parts by weight, more preferably 3 to 100 parts by weight and much more preferably 5 to 50 parts by weight based on 100 parts by weight of the organic phosphorus compound (component A).

Optionally, various auxiliary agents such as a bacteria/bug repellant, antistatic agent, light resistance accelerator, heat resistance accelerator, crosslinking agent, colorant, defoaming agent and flameproofing aid and fillers such as clay, talc, mica, swellable graphite; wollastonite, kaolin, montmorillonite, bentonite, sepiolite, zonotlite and silica may be added to the flameproofing agent of the present invention.

(Process for Manufacturing a Flameproof Fiber Product)

A description is subsequently given of a process for manufacturing a flameproof fiber product by using the organic phosphorus compound (component A).

A flameproofing agent for fibers comprising 100 parts by weight of a dispersant and 1 to 300 parts by weight of the organic phosphorus compound (component A) represented by the above formula (1) is first prepared.

Water, an organic solvent or a resin (including a solution, emulsion and latex) is preferred as the dispersant as described above.

To prepare the flameproofing agent, the organic phosphorus compound (component A) is preferably mixed with and dispersed in water, an organic solvent, or a resin solution, resin emulsion or latex. The above-described surfactant, stabilizer and another flameproofing agent may be optionally used.

At this point, the amount of the organic phosphorus compound (component A) to be mixed is preferably 5 to 200 parts by weight, more preferably 10 to 100 parts by weight and particularly preferably 20 to 50 parts by weight based on 100 parts by weight of the dispersant. When the amount of the organic phosphorus compound (component A) is smaller than 1 part by weight, the flameproofing effect may become unsatisfactory and when the amount is larger than 300 parts by weight, the formation of a resin film tends to become difficult and a fiber product may deteriorate in quality.

A flameproof fiber product is manufactured by adhering the obtained flameproofing agent to a fiber product in an amount of 3 to 150 wt % as a solid content. The solid content is preferably 7 to 100 wt %, particularly preferably 15 to 70 wt %. When the solid content is lower than 3 wt %, the flameproofing effect becomes unsatisfactory and when the solid content is higher than 150 wt %, a fiber product deteriorates in quality disadvantageously. The processing method is not particularly limited, and conventional immersion, spray, brush coating, exhaustion (dying and bathing method) and thermo-sol methods are generally employed.

The fiber product is not particularly limited, and typical examples thereof include curtains, carpets, rugs, artificial lawn, wall covering materials, chair upholstery, hangings (such as woven flags), car sheets, car mats, nonwoven filters, artificial leathers and electromagnetic shield materials. The type of the fiber material is not particularly limited, and typical examples thereof include synthetic fibers such as polyester, nylon, acrylonitrile and polypropylene, cellulose-based fibers such as rayon, cotton and hemp, and animal fibers such as wool, silk and feather. They may be used alone or in combination.

(Method of Improving Weatherability)

The present invention is a method of improving the weatherability of a flameproof fiber product obtained by adhering a flameproofing agent to a fiber product, wherein (i) the method comprises the step of adhering the flameproofing agent to the fiber product in an amount of 3 to 150 wt % as a solid content; and (ii) the flameproofing agent comprises 1 to 300 parts by weight of an organic phosphorus compound represented by the above formula (1) (component A) based on 100 parts by weight of a dispersant.

According to the present invention, not only the flameproofness but also the weatherability of a fiber product can be improved.

EXAMPLES

The following examples are provided for the purpose of further illustrating the present invention but are in no way to be taken as limiting. "Parts" and "%" mean "parts by weight" and "wt %", respectively, and evaluations were made by the following methods.

(1) Flameproofness 1

Flameproofness was evaluated based on FMVSS-302. For evaluation, the combustion distance from a bench mark, the combustion time from the time when a flame passed the bench mark and the combustion speed from the time when a flame passed the bench mark were measured three times each. "not burn" means that the flame is extinguished by itself below the bench mark and "slow burn" means that the flame is extinguished by itself 5 cm or less within 60 seconds after it passes the bench mark. A sample having a combustion speed of more than 10 cm/min is rejected.

(2) Flameproofness 2

The char length was measured by the 45° air-mixing burner metal net method of Fire Defense Law. When a specimen has a maximum char length of not more than 7 cm and an average char length of not more than 5 cm, its flameproofness is acceptable.

(3) Flameproofness 3

A flameproofness evaluation test was conducted in accordance with JIS L-1091 A-1 (micro-burner method) and JIS L-1091 D (45° coil method). According to the micro-burner method, when a specimen has an afterflaming time of 3 seconds or less, a glowing time of 5 seconds or less and a char area of 30 cm$^2$ or less in the 1-minute heating method and the 3-second heating method after flaming, its flameproofness is acceptable, and when a specimen has 3 or more times of flame contact in the 45° coil method, its flameproofness is acceptable.

(4) Flameproofness 4

This was evaluated based on the HB method specified in UL-94 of the American UL standards.

(5) Light Resistance

As for light resistance, the degree of discoloration after 200 hours of exposure at 83° C. was determined with a fade meter. (JIS-L0842, carbon arc lighting method; the degree of discoloration was determined with a blue scale for JIS discoloration)

(6) Heat Resistance

As for heat resistance, the degree of discoloration after the specimen was treated at 150° C. for 60 minutes in a gear oven drier was evaluated based on the following criteria.
○: not discolored
Δ: discolored (7) Texture The texture was determined by touch with hand.

(8) Acid Value

This was measured in accordance with JIS-K-3504.

Preparation Example 1: Preparation of 2,4,8,10-tetraoxa-3,9-diphosphaspiro[5.5]undecane,3,9-dibenzyl-3,9-dioxide (FR-1)

22.55 g (0.055 mole) of 3,9-dibenzyloxy-2,4,8,10-tetraoxa-3,9-diphosphaspiro[5.5]undecane, 19.01 g (0.11 mole) of benzyl bromide and 33.54 g (0.32 mole) of xylene were charged into a reactor having a stirrer, a thermometer and a condenser, and dry nitrogen was let flow into the reactor while they were stirred at room temperature. Then, heating was started with an oil bath to heat the above mixture at a reflux temperature (about 130° C.) for 4 hours under agitation. After the end of heating, the resulting mixture was left to be cooled to room temperature, and 20 mL of xylene was added and further stirred for another 30 minutes. The precipitated crystal was separated by filtration and washed with 20 mL of xylene twice. The obtained roughly purified product and 40 mL of methanol were injected into a reactor equipped with a condenser and a stirrer to be refluxed for about 2 hours. After the crystal was cooled to room temperature, it was separated by filtration and washed with 20 mL of methanol, and the obtained filtrate was dried at 120° C. and $1.33 \times 10^2$ Pa for 19 hours to obtain a white flaky crystal. It was confirmed by mass spectral analysis, $^1$H and $^{31}$P nuclear magnetic resonance spectral analysis and elemental analysis that the product was bisbenzyl pentaerythritol diphosphonate. The yield was 20.60 g, the yield rate was 91%, and the $^{31}$PNMR purity was 99%. The HPLC purity measured by the method described in this text was 99%. The acid value was 0.05 mgKOH/g.

$^1$H-NMR (DMSO-d$_6$, 300 MHz): δ7.2-7.4 (m, 10H, 4.1-4.5 (m, 8H), 3.5 (d, 4H), $^{31}$P-NMR (DMSO-d$_6$, 120 MHz): δ23.1 (S), melting point: 257° C., average particle diameter: 30 μm.

2,4,8,10-tetraoxa-3,9-diphosphaspiro[5,5]undecane, 3,9-dibenzyl-3,9-dioxide {phosphorus-based compound of the formula (1-a) (to be referred to as "FR-1" hereinafter)} synthesized in Preparation Example 1 was used as the organic phosphorus compound (component A) used in Examples.

Example 1 and Comparative Examples 1 and 2

After a car sheet fabric for car interior was coated with the following processing liquid, its flameproofness and physical properties were tested.

(tested fabric): polyester 100% woven car sheet fabric (weight of 300 g/m$^2$)

(processing agent): 1.5 parts of a nonionic surfactant, 1 part of a polyacrylic acid-based thickener and 0.5 part of 25% ammonia water were added to 100 parts of a polyacrylic acid ester emulsion having a solid content of 45%, and 30 parts of FR-1 was added under agitation. For comparison, trisdichloropropyl phosphate (Comparative Example 1) and a mixture of 75% of decabromodiphenyl ether and 25% of antimony trioxide (Comparative Example 2) were used in place of FR-1.

(processing method): Coating was carried out with a doctor knife. The amount of the solid matter adhered of the processing agent (processing liquid) was 100 g/m$^2$. Predrying was carried out at 80° C. for 5 minutes, and curing was carried out at 150° C. for 1 minute.

(test results): Flameproofness (evaluation of flameproofness 1) is shown in Table 1, and physical properties are shown in Table 2.

TABLE 1

| | Flameproofness test (FMVSS-302) | | | | | | | | |
|---|---|---|---|---|---|---|---|---|---|
| | n = 1 | | | n = 2 | | | n = 3 | | |
| Samples | Distance (mm) | Time (sec) | Speed (cm/min) | Distance (mm) | Time (sec) | Speed (cm/min) | Distance (mm) | Time (sec) | Speed (cm/min) |
| Ex. 1 | 0 | 0 | Not burn | 0 | 0 | Not burn | 0 | 0 | Not burn |
| C. Ex. 1 | 145 | 184 | 4.7 | 172 | 210 | 4.9 | 144 | 198 | 4.4 |
| C. Ex. 2 | 6 | 12 | Slow burn | 0 | 0 | Not burn | 3 | 7 | Slow burn |
| Unprocessed | 240 | 102 | 14.1 | 236 | 122 | 11.6 | 240 | 118 | 12.2 |

Ex.: Example, C. Ex.: Comparative Example

TABLE 2

| Samples | Light resistance | Heat resistance | Texture |
|---|---|---|---|
| Example 1 | Grade 4 to 5 | ○ | Good |
| Comparative Example 1 | Grade 3 to 4 | Δ | Slightly tacky |
| Comparative Example 2 | Grade 4 | Δ | Slightly hard |
| Unprocessed | Grade 4 to 5 | ○ | Good |

Example 2 and Comparative Example 3

After a side fabric for chair upholstery was coated with the following processing liquid, its flameproofness and physical properties were tested.

(tested fabric): commercially available polyester 100% jersey fabric (weight of 140 g/m$^2$)

(processing agent): 30 parts of FR-1 and 5 parts of a carboxymethyl cellulose thickener (70% aqueous solution) were added to 100 parts of a polyurethane resin emulsion having a solid content of 50% under agitation. As Comparative Example 3, a mixed solution of 60% of zinc borate and 40% of aluminum hydroxide was used.

(processing method): same as in Example 1

(test results): Flameproofness (evaluation of flameproofness 2) is shown in Table 3, and physical properties are shown in Table 4.

TABLE 3

| | Test by 45° air-mixing burner metal net method specified by Fire Defense Law Char length (cm) | | |
|---|---|---|---|
| Samples | n = 1 | n = 2 | n = 3 |
| Example 2 | 3.2 | 3.4 | 3.7 |
| Comparative Example 3 | ∞ | ∞ | ∞ |
| Unprocessed | ∞ | ∞ | ∞ |

TABLE 4

| Samples | Light resistance | Heat resistance | Texture |
|---|---|---|---|
| Example 2 | Grade 4 | ○ | Good |
| Comparative Example 2 | Grade 4 | ○ | Slightly hard |
| Unprocessed | Grade 4 | ○ | Good |

Example 3 and Comparative Example 4

After a polyester nonwoven filter was sprayed with the following processing liquid, its flameproofness and physical properties were tested.

(tested fabric): polyester 100% nonwoven fabric (weight of 50 g/m$^2$)

(processing agent): 1.5 parts of a nonionic surfactant, 1 part of a polyacrylic acid-based thickener and 0.5 part of 25% ammonia water were added to 100 parts of a polyacrylic acid ester resin emulsion having a solid content of 45%, and 45 parts of a water dispersion of FR-1 having an average particle diameter of not more than 10 μm prepared by using a bead mill was added as a solid content under agitation. As Comparative Example 4, aluminum hydroxide (average particle diameter of 100 μm) was used in place of FR-1.

(processing method): The filter was sprayed. In the spraying method, the amount of the solid matter adhered of the processing agent (processing liquid) was 20 g/m$^2$ on one side and 40 g/m$^2$ on both sides. Pre-drying was carried out at 80° C. for 5 minutes, and curing was carried out at 150° C. for 1 minute.

(test results): Flameproofness (evaluation of flameproofness 3) is shown in Table 5, and physical properties are shown in Table 6.

TABLE 5

Flameproofness test(JIS-L1091)

| Sample | One-minute heating of A-1 method | | | Three-second heating after catching a flame of A-1 method | | | Coil method |
|---|---|---|---|---|---|---|---|
| | Afterflaming (sec) | Glowing (sec) | char area (cm$^2$) | Afterflaming (sec) | Glowing (sec) | char area (cm$^2$) | Number of flame contacts |
| Example 3 | 0 | 0 | 5.5 | 0 | 0 | 4.8 | 4 |
| Comparative Example 4 | Totally burnt | | | Totally burnt | | | 1 |

TABLE 6

| Sample | Texture |
|---|---|
| Example 3 | Good |
| Comparative Example 4 | Slightly hard |

Example 4 and Comparative Example 5

After a pongee fabric for woven flags was coated with the following processing liquid, its flameproofness and physical properties were tested.

(tested fabric): commercially available polyester 100% pongee fabric (weight of 60 g/m$^2$)

(processing agent): 40 parts of FR-1 and 40 parts of water were added to 100 parts of polyacrylic acid ester resin paste having a solid content of 50% under agitation. As Comparative Example 5, silica coated ammonium polyphosphate (average particle diameter of 30 μm, FRCROS486 (trade name) of Chemische Fabrik Budenheim) was used.

(processing method): same as in Example 1. The amount of the solid matter adhered of the processing agent (processing liquid) was 20 g/m$^2$. Pre-drying was carried out at 80° C. for 5 minutes, and curing was carried out at 150° C. for 1 minute.

(test results): Flameproofness (evaluation of flameproofness 3) is shown in Table 7, and physical properties are shown in Table 8.

TABLE 7

Flameproofness test(JIS-L1091: after immersing in water at 50° C. for 30 min.)

| Sample | One-minute heating of A-1 method | | | Three-second heating after catching a flame of A-1 method | | | Coil method |
|---|---|---|---|---|---|---|---|
| | Afterflaming (sec) | Glowing (sec) | char area (cm$^2$) | Afterflaming (sec) | Glowing (sec) | char area (cm$^2$) | Number of flame contacts (contacts) |
| Example 4 | 0 | 0 | 4.5 | 0 | 0 | 4.0 | 4 |
| Comparative Example 5 | Totally burnt | | | Totally burnt | | | 1 |

TABLE 8

| Sample | Texture |
|---|---|
| Example 4 | Good |
| Comparative Example 5 | Slightly slimy on surface |

Example 5 and Comparative Example 6

After an electromagnetic shield substrate was immersed in the following processing liquid, its flameproofness and physical properties were tested.

(tested fabric): electromagnetic shield substrate urethane foam plated with copper (weight of 100 g/m$^2$)

(processing agent): 50 parts of FR-1 and 50 parts of water were added to 100 parts of polyurethane resin paste having a solid content of 50% under agitation. As Comparative Example 6, silica coated ammonium polyphosphate (average particle diameter of 30 μm, FRCROS486 (trade name) of Chemische Fabrik Budenheim) was used.

(processing method): The electromagnetic shield substrate was immersed. The amount of the solid matter adhered of the processing agent (processing liquid) was 50 g/m$^2$. Pre-drying was carried out at 80° C. for 5 minutes, and curing was carried out at 150° C. for 1 minute.

(test results): Flameproofness (evaluation of flameproofness 4) is shown in Table 9.

TABLE 9

| | Flameproofness test(UL-94 HB method) | | | | | | | | |
|---|---|---|---|---|---|---|---|---|---|
| | n = 1 | | | n = 2 | | | n = 3 | | |
| Sample | Distance (mm) | Time (sec) | Speed (cm/min) | Distance (mm) | Time (sec) | Speed (cm/min) | Distance (mm) | Time (sec) | Speed (cm/min) |
| Example 5 | Below bench mark | | | Below bench mark | | | Below bench mark | | |
| Comparative Example 6 | 9 | 10 | 5.4 | 10 | 10 | 6.0 | 9 | 10 | 5.4 |
| Unprocessed | 75 | 22 | 20.5 | 75 | 28 | 16.1 | 75 | 25 | 18.0 |

Examples 6 and 7 and Comparative Example 7

After a car sheet fabric for car interior was coated with the following processing liquid, FMVSS-302 method evaluation was made, and physical properties were tested.
(tested fabric): polyester 100% woven car sheet fabric (weight of 200 g/m$^2$)
(flameproofing agent) 50 parts of FR-1 was added to a homogeneous mixed solution of 5 parts of a polyoxyethylenedistyrenated phenol ether sulfuric acid salt, 1 part of hardened castor oil and 42.5 parts of water, the resulting mixture was milled and dispersed by means of a bead mill (using glass beads having a diameter of 1.0 to 1.4 mm, manufactured by IMEX Co., Ltd.) at a revolution of 2,000 rpm for a milling time of 3 hours in accordance with a circulation system to obtain a homogeneous white dispersion, and 1 part of a polyacrylic acid-based thickener and 0.5 part of 25% ammonia water were added to obtain a flameproofing agent. When the average particle diameter of the obtained flameproofing agent was measured by means of a particle size distribution measuring instrument (LA-910 laser diffraction/scattering particle size distribution measuring instrument of Horiba, Ltd.), it was 3.2 μm. This is designated as flameproofing agent-(1) (Example 6. No. 1). For comparison, a homogeneous white dispersion-like flameproofing agent was obtained by milling and dispersing melamine polyphosphate in place of FR-1 in the same manner as the flameproofing agent-(I). This is designated as flameproofing agent-(II) (Comparative Example 7, No. 2). The average particle diameter of the flameproofing agent-(II) was 5.1 μm. Further, a mixture of 70 parts of the flameproofing agent-(I) and 30 parts of the flameproofing agent-(II) is designated as flameproofing agent-(III) (Example 7, No. 3).
(processing liquid): 2 parts of a polyacrylic acid-based thickener and 1 part of 25% ammonia water were added to 100 parts of an urethane resin emulsion having a solid content of 40%, and 60 parts of the flameproofing agent was added to the resulting mixture under agitation.
(processing method): The obtained flameproofing agent was coated with a doctor knife. The amount of the solid matter adhered of the processing liquid was 120 g/m$^2$. Pre-drying was carried out at 80° C. for 5 minutes, and curing was carried out at 150° C. for 1 minute. The amount of the solid matter after drying of the processed fabric is shown in Table 10.
(testing method): The FMVSS-302 method was used to evaluate flameproofness, and light resistance, heat resistance and texture were judged.
(test results) Flameproofness is shown in Table 11, and physical properties are shown in Table 12. A test specimen having a combustion speed higher than 10 cm/min, was rejected.

TABLE 10

| | Amount of solid content after drying(g/m$^2$) | | |
|---|---|---|---|
| Samples | Solid content of urethane resin | FR-1 | Melamine polyphosphate |
| Example 6 | 68.6 | 51.4 | — |
| Comparative Example 7 | 68.6 | — | 51.4 |
| Example 7 | 68.6 | 36.0 | 15.4 |

TABLE 11

| | Flameproofness test(FMVSS-302) | | | | | | | | |
|---|---|---|---|---|---|---|---|---|---|
| | n = 1 | | | n = 2 | | | n = 3 | | |
| Samples | Distance (mm) | Time (sec) | Speed (cm/min) | Distance (mm) | Time (sec) | Speed (cm/min) | Distance (mm) | Time (sec) | Speed (cm/min) |
| Example 6 | 2 | 5 | Hardly burnt | 5 | 3 | Hardly burnt | 0 | 0 | not burnt |
| Comparative Example 7 | 128 | 155 | 5.0 | 155 | 163 | 5.7 | 149 | 158 | 5.7 |
| Example 7 | 0 | 0 | not burnt | 0 | 0 | not burnt | 0 | 0 | not burnt |
| Unprocessed | 250 | 98 | 15.3 | 245 | 88 | 16.7 | 250 | 94 | 16.0 |

Not burnt: self-extinguished below bench mark
Hardly burnt: self-extinguished 5 cm or less across bench mark within 1 minute

TABLE 12

| Samples | Light resistance | Heat resistance | Texture |
|---|---|---|---|
| Example 6 | Grade 4 to 5 | ○ | Good |
| Comparative Example 7 | Grade 4 to 5 | ○ | Good |
| Example 7 | Grade 4 to 5 | ○ | Good |
| Unprocessed | Grade 4 to 5 | ○ | Good |

EFFECT OF THE INVENTION

According to the present invention, a fiber product can be flameproofed without using a halogen-based flameproofing agent. In addition, a fireproof fiber product obtained by the present invention does not deteriorate in light resistance, heat resistance and texture.

INDUSTRIAL APPLICABILITY

The flameproofing agent for fibers of the present invention is useful as a processing agent for fireproof fiber products.

The invention claimed is:

1. A flameproofing agent for fibers comprising:
   (A) an organic phosphorus compound of the following formula (1-a),

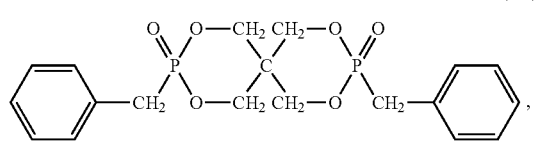

(1-a)

having an average particle diameter of 10 to 50 μm, an HPLC purity of at least 99%, and an acid value of not more than 0.7 mgKOH/g,
   (B) a dispersant comprising water and a resin selected from the group consisting of (i) a polyacrylic acid ester, (ii) a polymethacrylic acid ester, and (iii) a copolymer of an acrylic acid ester and/or a methacrylic acid ester and a vinyl-based monomer or an olefinic monomer, and
   (C) 0.1 to 10 parts by weight of an emulsification stabilizer of sodium polyacrylate, based on 100 parts by weight of the dispersant.

2. The flameproofing agent for fibers according to claim 1, which comprises 100 parts by weight of the dispersant and 1 to 300 parts by weight of the organic phosphorus compound of formula (1-a).

3. The flameproofing agent for fibers according to claim 1, which further comprises 1 to 30 parts by weight of a surfactant based on 100 parts by weight of the dispersant.

4. The flameproofing agent for fibers according to claim 1, which further comprises 1 to 200 parts by weight of at least one compound selected from the group consisting of aluminum hydroxide, titanium oxide, zinc oxide, swellable graphite, magnesium hydroxide, calcium carbonate, zinc borate, melamine, red phosphorus, ammonium polyphosphate, melamine polyphosphate, melamine cyanurate and a phosphoric acid ester based on 100 parts by weight of the organic phosphorus compound of formula (1-a).

5. A process for manufacturing a flameproof fiber product, comprising adhering a flameproofing agent comprising:
   (A) 1 to 300 parts by weight of an organic phosphorus compound of the following formula (1-a)

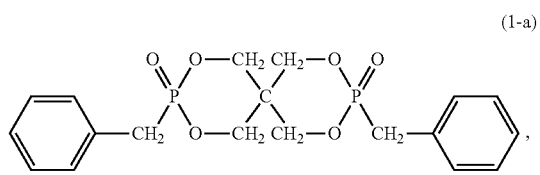 [SMILES: O=P1(Cc2ccccc2)OCC2(CO1)COP(=O)(Cc1ccccc1)OC2]

(1-a)

having an average particle diameter of 10 to 50 μm, an HPLC purity of at least 99%, and an acid value of not more than 0.7 mgKOH/g,
   (B) 100 parts by weight of a dispersant comprising water and a resin selected from the group consisting of (i) a polyacrylic acid ester, (ii) a polymethacrylic acid ester, and (iii) a copolymer of an acrylic acid ester and/or a methacrylic acid ester and a vinyl-based monomer or an olefinic monomer, and
   (C) 0.1 to 10 parts by weight of an emulsification stabilizer of sodium polyacrylate, based on 100 parts by weight of the dispersant,
   to a fiber product in an amount of 3 to 150 wt % as a solid content.

6. A flameproof fiber product obtained by the manufacturing process of claim 5.

7. A method of improving the weatherability of a flameproof fiber product obtained by adhering a flameproofing agent to a fiber product, wherein
   (i) the method comprises a step of adhering the flameproofing agent to the fiber product in an amount of 3 to 150 wt % as a solid content; and
   (ii) the flameproofing agent comprises:
   (A) 1 to 300 parts of an organic phosphorus compound of the following formula (1-a)

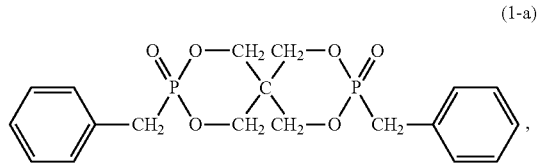 [SMILES: O=P1(Cc2ccccc2)OCC2(CO1)COP(=O)(Cc1ccccc1)OC2]

(1-a)

having an average particle diameter of 10 to 50 μm, an HPLC purity of at least 99%, and an acid value of not more than 0.7 mgKOH/g,
   (B) 100 parts by weight of a dispersant comprising water and a resin selected from the group consisting of (i) a polyacrylic acid ester, (ii) a polymethacrylic acid ester, and (iii) a copolymer of an acrylic acid ester and/or a methacrylic acid ester and a vinyl-based monomer or an olefinic monomer, and
   (C) 0.1 to 10 parts by weight of an emulsification stabilizer of sodium polyacrylate, based on 100 parts by weight of the dispersant.

8. The flameproofing agent for fibers according to claim 1, which comprises 100 parts by weight of the resin and 5 to 300 parts by weight of the organic phosphorus compound of formula (1-a).

9. The flameproofing agent for the fibers according to claim 3, wherein the surfactant is at least one selected from the group consisting of an anionic surfactant and a nonionic surfactant.

\* \* \* \* \*